(12) United States Patent
Bonhoeffer

(10) Patent No.: US 10,245,142 B2
(45) Date of Patent: Apr. 2, 2019

(54) MULTIPLE ORIFICE IMPLANTABLE HEART VALVE AND METHODS OF IMPLANTATION

(71) Applicant: Medtronic, Inc., Minneapolis, MN (US)

(72) Inventor: Philipp Bonhoeffer, London (GB)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 14/723,930

(22) Filed: May 28, 2015

(65) Prior Publication Data

US 2016/0278916 A1  Sep. 29, 2016

Related U.S. Application Data

(63) Continuation of application No. 13/860,779, filed on Apr. 11, 2013, now abandoned, which is a continuation of application No. 12/364,246, filed on Feb. 2, 2009, now Pat. No. 8,430,927.

(60) Provisional application No. 61/123,337, filed on Apr. 8, 2008.

(51) Int. Cl.
*A61F 2/24* (2006.01)

(52) U.S. Cl.
CPC .......... *A61F 2/2409* (2013.01); *A61F 2/2418* (2013.01); *A61F 2/2427* (2013.01); *A61F 2220/0008* (2013.01); *A61F 2220/0016* (2013.01); *A61F 2230/001* (2013.01); *A61F 2230/0006* (2013.01); *A61F 2230/0008* (2013.01); *A61F 2230/0032* (2013.01); *A61F 2230/0034* (2013.01)

(58) Field of Classification Search
CPC ......... A61F 2/24; A61F 2/2409; A61F 2/2418
See application file for complete search history.

(56) References Cited

U.S. PATENT DOCUMENTS

| 3,334,629 A | 8/1967 | Cohn |
| 3,409,013 A | 11/1968 | Berry |
| 3,540,431 A | 11/1970 | Mobin-Uddin |

(Continued)

FOREIGN PATENT DOCUMENTS

| CN | 2007-100074433 | 8/2007 |
| DE | 3640745 | 6/1987 |

(Continued)

OTHER PUBLICATIONS

Andersen, H.R. et al, "Transluminal implantation of artificial heart valves. Description of a new expandable aortic valve and initial results with implantation by catheter technique in closed chest pigs." Euro. Heart J. (1992) 13:704-708.

(Continued)

*Primary Examiner* — Suba Ganesan
(74) *Attorney, Agent, or Firm* — Dicke, Billig & Czaja, PLLC

(57) ABSTRACT

A surgically implantable multiple orifice heart valve having a valve frame with at least two orifices, each of which can accommodate a tissue valve. The multiple orifice heart valve includes a stent frame having a first side, an opposite second side, and multiple orifices or opening, each of which extends from the first side to the second side of the stent frame and is adjacent to at least one of the other multiple orifices or openings.

13 Claims, 3 Drawing Sheets

(56) References Cited

U.S. PATENT DOCUMENTS

| | | |
|---|---|---|
| 3,587,115 A | 6/1971 | Shiley |
| 3,628,535 A | 12/1971 | Ostrowsky et al. |
| 3,642,004 A | 2/1972 | Osthagen et al. |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 3,795,246 A | 3/1974 | Sturgeon |
| 3,839,741 A | 10/1974 | Haller |
| 3,868,956 A | 3/1975 | Alfidi et al. |
| 3,874,388 A | 4/1975 | King et al. |
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,233,690 A | 11/1980 | Akins |
| 4,265,694 A | 5/1981 | Boretos |
| 4,291,420 A | 9/1981 | Reul |
| 4,297,749 A | 11/1981 | Davis et al. |
| 4,339,831 A | 7/1982 | Johnson |
| 4,343,048 A | 8/1982 | Ross et al. |
| 4,345,340 A | 8/1982 | Rosen |
| 4,425,908 A | 1/1984 | Simon |
| 4,470,157 A | 9/1984 | Love |
| 4,501,030 A | 2/1985 | Lane |
| 4,574,803 A | 3/1986 | Storz |
| 4,580,568 A | 4/1986 | Gianturco |
| 4,592,340 A | 6/1986 | Boyles |
| 4,610,688 A | 9/1986 | Silvestrini et al. |
| 4,612,011 A | 9/1986 | Kautzky |
| 4,647,283 A | 3/1987 | Carpentier et al. |
| 4,648,881 A | 3/1987 | Carpentier et al. |
| 4,655,771 A | 4/1987 | Wallsten |
| 4,662,885 A | 5/1987 | DiPisa, Jr. |
| 4,665,906 A | 5/1987 | Jervis |
| 4,681,908 A | 7/1987 | Broderick et al. |
| 4,710,192 A | 12/1987 | Liotta et al. |
| 4,733,665 A | 3/1988 | Palmaz |
| 4,777,951 A | 10/1988 | Cribier et al. |
| 4,781,716 A | 11/1988 | Richelsoph |
| 4,787,899 A | 11/1988 | Lazarus |
| 4,796,629 A | 1/1989 | Grayzel |
| 4,797,901 A | 1/1989 | Baykut |
| 4,819,751 A | 4/1989 | Shimada et al. |
| 4,834,755 A | 5/1989 | Silvestrini et al. |
| 4,856,516 A | 8/1989 | Hillstead |
| 4,872,874 A | 10/1989 | Taheri |
| 4,878,495 A | 11/1989 | Grayzel |
| 4,878,906 A | 11/1989 | Lindemann et al. |
| 4,883,458 A | 11/1989 | Shiber |
| 4,902,291 A | 2/1990 | Kolff |
| 4,909,252 A | 3/1990 | Goldberger |
| 4,917,102 A | 4/1990 | Miller et al. |
| 4,922,905 A | 5/1990 | Strecker |
| 4,954,126 A | 9/1990 | Wallsten |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,002,559 A | 3/1991 | Tower |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,059,177 A | 10/1991 | Towne et al. |
| 5,061,273 A | 10/1991 | Yock |
| 5,085,635 A | 2/1992 | Cragg |
| 5,089,015 A | 2/1992 | Ross |
| 5,135,539 A | 8/1992 | Carpentier |
| 5,152,771 A | 10/1992 | Sabbaghian et al. |
| 5,161,547 A | 11/1992 | Tower |
| 5,163,953 A | 11/1992 | Vince |
| 5,167,628 A | 12/1992 | Boyles |
| 5,217,483 A | 7/1993 | Tower |
| 5,232,445 A | 8/1993 | Bonzel |
| 5,272,909 A | 12/1993 | Nguyen et al. |
| 5,295,958 A | 3/1994 | Shturman |
| 5,327,774 A | 7/1994 | Nguyen et al. |
| 5,332,402 A | 7/1994 | Teitelbaum et al. |
| 5,350,398 A | 9/1994 | Pavcnik et al. |
| 5,370,685 A | 12/1994 | Stevens |
| 5,389,106 A | 2/1995 | Tower |
| 5,397,351 A | 3/1995 | Pavcnik et al. |
| 5,411,552 A | 5/1995 | Andersen et al. |
| 5,415,633 A | 5/1995 | Lazarus et al. |
| 5,431,676 A | 7/1995 | Dubrul et al. |
| 5,443,446 A | 8/1995 | Shturman |
| 5,449,384 A | 9/1995 | Johnson |
| 5,480,424 A | 1/1996 | Cox |
| 5,489,294 A | 2/1996 | McVenes et al. |
| 5,489,297 A | 2/1996 | Duran |
| 5,496,346 A | 3/1996 | Horzewski et al. |
| 5,500,014 A | 3/1996 | Quijano et al. |
| 5,507,767 A | 4/1996 | Maeda et al. |
| 5,545,209 A | 8/1996 | Roberts et al. |
| 5,545,211 A | 8/1996 | An et al. |
| 5,545,214 A | 8/1996 | Stevens |
| 5,554,185 A | 9/1996 | Block et al. |
| 5,575,818 A | 11/1996 | Pinchuk |
| 5,580,922 A | 12/1996 | Park et al. |
| 5,591,195 A | 1/1997 | Taheri et al. |
| 5,609,626 A | 3/1997 | Quijano et al. |
| 5,645,559 A | 7/1997 | Hachtman et al. |
| 5,665,115 A | 9/1997 | Cragg |
| 5,667,523 A | 9/1997 | Bynon et al. |
| 5,674,277 A | 10/1997 | Freitag |
| 5,695,498 A | 12/1997 | Tower |
| 5,702,368 A | 12/1997 | Stevens et al. |
| 5,713,953 A | 2/1998 | Vallana et al. |
| 5,716,417 A | 2/1998 | Girard et al. |
| 5,746,709 A | 5/1998 | Rom et al. |
| 5,749,890 A | 5/1998 | Shaknovich |
| 5,766,151 A | 6/1998 | Valley et al. |
| 5,782,809 A | 7/1998 | Umeno et al. |
| 5,800,456 A | 9/1998 | Maeda et al. |
| 5,800,508 A | 9/1998 | Goicoechea et al. |
| 5,817,126 A | 10/1998 | Imran |
| 5,824,041 A | 10/1998 | Lenker |
| 5,824,043 A | 10/1998 | Cottone, Jr. |
| 5,824,053 A | 10/1998 | Khosravi et al. |
| 5,824,056 A | 10/1998 | Rosenberg |
| 5,824,061 A | 10/1998 | Quijano et al. |
| 5,824,064 A | 10/1998 | Taheri |
| 5,840,081 A | 11/1998 | Andersen et al. |
| 5,843,158 A | 12/1998 | Lenker et al. |
| 5,851,232 A | 12/1998 | Lois |
| 5,855,597 A | 1/1999 | Jayaraman |
| 5,855,601 A | 1/1999 | Bessler et al. |
| 5,860,996 A | 1/1999 | Tower |
| 5,861,028 A | 1/1999 | Angell |
| 5,868,783 A | 2/1999 | Tower |
| 5,876,448 A | 3/1999 | Thompson et al. |
| 5,888,201 A | 3/1999 | Stinson et al. |
| 5,891,191 A | 4/1999 | Stinson |
| 5,906,619 A | 5/1999 | Olson et al. |
| 5,907,893 A | 6/1999 | Zadno-Azizi et al. |
| 5,913,842 A | 6/1999 | Boyd et al. |
| 5,925,063 A | 7/1999 | Khosravi |
| 5,944,738 A | 8/1999 | Amplatz et al. |
| 5,957,949 A | 9/1999 | Leonhardt et al. |
| 5,968,068 A | 10/1999 | Dehdashtian et al. |
| 5,984,957 A | 11/1999 | Laptewicz, Jr. et al. |
| 5,997,573 A | 12/1999 | Quijano et al. |
| 6,022,370 A | 2/2000 | Tower |
| 6,027,525 A | 2/2000 | Suh et al. |
| 6,029,671 A | 2/2000 | Stevens et al. |
| 6,042,589 A | 3/2000 | Marianne |
| 6,042,598 A | 3/2000 | Tsugita et al. |
| 6,042,607 A | 3/2000 | Williamson, IV |
| 6,051,104 A | 4/2000 | Jang |
| 6,059,809 A | 5/2000 | Amor et al. |
| 6,110,201 A | 8/2000 | Quijano et al. |
| 6,146,366 A | 11/2000 | Schachar |

(56) References Cited

U.S. PATENT DOCUMENTS

| | | |
|---|---|---|
| 6,159,239 A | 12/2000 | Greenhalgh |
| 6,162,208 A | 12/2000 | Hipps |
| 6,162,245 A | 12/2000 | Jayaraman |
| 6,168,614 B1 | 1/2001 | Andersen et al. |
| 6,171,335 B1 | 1/2001 | Wheatley et al. |
| 6,200,336 B1 | 3/2001 | Pavcnik et al. |
| 6,203,550 B1 | 3/2001 | Olson |
| 6,210,408 B1 | 4/2001 | Chandrasekaran et al. |
| 6,218,662 B1 | 4/2001 | Tchakarov et al. |
| 6,221,006 B1 | 4/2001 | Dubrul et al. |
| 6,221,091 B1 | 4/2001 | Khosravi |
| 6,241,757 B1 | 6/2001 | An et al. |
| 6,245,102 B1 | 6/2001 | Jayaraman |
| 6,248,116 B1 | 6/2001 | Chevilon |
| 6,258,114 B1 | 7/2001 | Konya et al. |
| 6,258,115 B1 | 7/2001 | Dubrul |
| 6,258,120 B1 | 7/2001 | McKenzie et al. |
| 6,277,555 B1 | 8/2001 | Duran et al. |
| 6,299,637 B1 | 10/2001 | Shaolia et al. |
| 6,302,906 B1 | 10/2001 | Goicoechea et al. |
| 6,309,382 B1 | 10/2001 | Garrison et al. |
| 6,309,417 B1 | 10/2001 | Spence et al. |
| 6,338,735 B1 | 1/2002 | Stevens |
| 6,348,063 B1 | 2/2002 | Yassour et al. |
| 6,350,277 B1 | 2/2002 | Kocur |
| 6,352,708 B1 | 3/2002 | Duran et al. |
| 6,371,970 B1 | 4/2002 | Khosravi et al. |
| 6,371,983 B1 | 4/2002 | Lane |
| 6,379,383 B1 | 4/2002 | Palmaz et al. |
| 6,380,457 B1 | 4/2002 | Yurek et al. |
| 6,398,807 B1 | 6/2002 | Chouinard et al. |
| 6,409,750 B1 | 6/2002 | Hyodoh et al. |
| 6,425,916 B1 | 7/2002 | Garrison et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,303 B1 | 10/2002 | Amplatz et al. |
| 6,475,239 B1 | 11/2002 | Campbell et al. |
| 6,482,228 B1 | 11/2002 | Norred |
| 6,488,704 B1 | 12/2002 | Connelly et al. |
| 6,494,909 B2 | 12/2002 | Greenhalgh |
| 6,503,272 B2 | 1/2003 | Duerig et al. |
| 6,508,833 B2 | 1/2003 | Pavcnik et al. |
| 6,527,800 B1 | 3/2003 | McGuckin, Jr. et al. |
| 6,530,949 B2 | 3/2003 | Konya et al. |
| 6,530,952 B2 | 3/2003 | Vesely |
| 6,562,031 B2 | 5/2003 | Chandrasekaran et al. |
| 6,562,058 B2 | 5/2003 | Seguin et al. |
| 6,569,196 B1 | 5/2003 | Vesely |
| 6,582,462 B1 | 6/2003 | Andersen et al. |
| 6,585,758 B1 | 7/2003 | Chouinard et al. |
| 6,592,546 B1 | 7/2003 | Barbut et al. |
| 6,605,112 B1 | 8/2003 | Moll et al. |
| 6,613,077 B2 | 9/2003 | Gilligan et al. |
| 6,622,604 B1 | 9/2003 | Chouinard et al. |
| 6,635,068 B1 | 10/2003 | Dubrul et al. |
| 6,652,571 B1 | 11/2003 | White et al. |
| 6,652,578 B2 | 11/2003 | Bailey et al. |
| 6,656,213 B2 | 12/2003 | Solem |
| 6,663,663 B2 | 12/2003 | Kim et al. |
| 6,669,724 B2 | 12/2003 | Park et al. |
| 6,673,089 B1 | 1/2004 | Yassour et al. |
| 6,673,109 B2 | 1/2004 | Cox |
| 6,676,698 B2 | 1/2004 | McGuckin, Jr. et al. |
| 6,682,558 B2 | 1/2004 | Tu et al. |
| 6,682,559 B2 | 1/2004 | Myers et al. |
| 6,685,739 B2 | 2/2004 | DiMatteo et al. |
| 6,689,144 B2 | 2/2004 | Gerberding |
| 6,689,164 B1 | 2/2004 | Seguin |
| 6,692,512 B2 | 2/2004 | Jang |
| 6,692,513 B2 | 2/2004 | Streeter et al. |
| 6,695,878 B2 | 2/2004 | McGuckin, Jr. et al. |
| 6,702,851 B1 | 3/2004 | Chinn et al. |
| 6,719,789 B2 | 4/2004 | Cox |
| 6,730,118 B2 | 5/2004 | Spenser et al. |
| 6,730,377 B2 | 5/2004 | Wang |
| 6,733,525 B2 | 5/2004 | Yang et al. |
| 6,736,846 B2 | 5/2004 | Cox |
| 6,752,828 B2 | 6/2004 | Thornton |
| 6,758,855 B2 | 7/2004 | Fulton, III et al. |
| 6,769,434 B2 | 8/2004 | Liddicoat et al. |
| 6,786,925 B1 | 9/2004 | Schoon |
| 6,790,229 B1 | 9/2004 | Berreklouw |
| 6,790,230 B2 | 9/2004 | Beyersdorf et al. |
| 6,792,979 B2 | 9/2004 | Konya et al. |
| 6,797,002 B2 | 9/2004 | Spence |
| 6,821,297 B2 | 11/2004 | Snyders |
| 6,830,575 B2 | 12/2004 | Stenzel et al. |
| 6,830,584 B1 | 12/2004 | Seguin |
| 6,830,585 B1 | 12/2004 | Artof |
| 6,846,325 B2 | 1/2005 | Liddicoat |
| 6,866,650 B2 | 3/2005 | Stevens |
| 6,872,223 B2 | 3/2005 | Roberts |
| 6,875,231 B2 | 4/2005 | Anduiza et al. |
| 6,883,522 B2 | 4/2005 | Spence et al. |
| 6,887,266 B2 | 5/2005 | Williams et al. |
| 6,890,330 B2 | 5/2005 | Streeter et al. |
| 6,893,460 B2 | 5/2005 | Spenser et al. |
| 6,896,690 B1 | 5/2005 | Lambrecht et al. |
| 6,908,481 B2 | 6/2005 | Cribier |
| 6,913,600 B2 | 7/2005 | Valley et al. |
| 6,929,653 B2 | 8/2005 | Streeter |
| 6,936,066 B2 | 8/2005 | Palmaz et al. |
| 6,939,365 B1 | 9/2005 | Fogarty et al. |
| 6,951,571 B1 | 10/2005 | Srivastava |
| 6,974,474 B2 | 12/2005 | Pavcnik et al. |
| 6,974,476 B2 | 12/2005 | McGuckin et al. |
| 6,986,742 B2 | 1/2006 | Hart et al. |
| 6,989,027 B2 | 1/2006 | Allen et al. |
| 6,989,028 B2 | 1/2006 | Lashinski et al. |
| 6,991,649 B2 | 1/2006 | Sievers |
| 7,018,401 B1 | 3/2006 | Hyodoh et al. |
| 7,041,128 B2 | 5/2006 | McGuckin, Jr. et al. |
| 7,044,966 B2 | 5/2006 | Svanidze et al. |
| 7,048,014 B2 | 5/2006 | Hyodoh et al. |
| 7,097,659 B2 | 8/2006 | Woolfson et al. |
| 7,101,396 B2 | 9/2006 | Artof et al. |
| 7,105,016 B2 | 9/2006 | Shui et al. |
| 7,105,020 B2 | 9/2006 | Greenberg et al. |
| 7,115,141 B2 | 10/2006 | Menz et al. |
| 7,128,759 B2 | 10/2006 | Osborne et al. |
| 7,147,663 B1 | 12/2006 | Berg et al. |
| 7,153,324 B2 | 12/2006 | Case et al. |
| 7,160,319 B2 | 1/2007 | Chouinard et al. |
| 7,175,656 B2 | 2/2007 | Khairkhahan |
| 7,179,290 B2 | 2/2007 | Cao |
| 7,186,265 B2 | 3/2007 | Sharkawy et al. |
| 7,195,641 B2 | 3/2007 | Palmaz et al. |
| 7,198,646 B2 | 4/2007 | Figulla et al. |
| 7,201,761 B2 | 4/2007 | Woolfson et al. |
| 7,201,772 B2 | 4/2007 | Schwammenthal et al. |
| 7,252,682 B2 | 8/2007 | Seguin |
| 7,300,457 B2 | 11/2007 | Palmaz |
| 7,300,463 B2 | 11/2007 | Liddicoat |
| 7,316,706 B2 | 1/2008 | Bloom et al. |
| 7,329,278 B2 | 2/2008 | Seguin |
| 7,335,218 B2 | 2/2008 | Wilson et al. |
| 7,338,520 B2 | 3/2008 | Bailey et al. |
| 7,374,571 B2 | 5/2008 | Pease et al. |
| 7,377,938 B2 | 5/2008 | Sarac et al. |
| 7,381,218 B2 | 6/2008 | Shreck |
| 7,384,411 B1 | 6/2008 | Condado |
| 7,429,269 B2 | 9/2008 | Schwammenthal et al. |
| 7,442,204 B2 | 10/2008 | Schwammenthal et al. |
| 7,462,191 B2 | 12/2008 | Spenser et al. |
| 7,470,284 B2 | 12/2008 | Lambrecht et al. |
| 7,481,838 B2 | 1/2009 | Carpentier et al. |
| 7,527,646 B2 | 5/2009 | Rahdert et al. |
| 7,544,206 B2 | 6/2009 | Cohn et al. |
| 7,547,322 B2 | 6/2009 | Sarac et al. |
| 7,556,646 B2 | 7/2009 | Yang et al. |
| 7,682,390 B2 | 3/2010 | Seguin |
| 7,780,726 B2 | 8/2010 | Seguin |

(56) References Cited

U.S. PATENT DOCUMENTS

| | | |
|---|---|---|
| 7,806,919 B2 | 10/2010 | Bloom et al. |
| 7,871,435 B2 | 1/2011 | Carpentier |
| 2001/0002445 A1 | 3/2001 | Vesely |
| 2001/0001314 A1 | 5/2001 | Davison et al. |
| 2001/0007956 A1 | 7/2001 | Letac et al. |
| 2001/0010017 A1 | 7/2001 | Letac et al. |
| 2001/0011189 A1 | 8/2001 | Drasler et al. |
| 2001/0021872 A1* | 9/2001 | Bailey .............. A61F 2/2418 623/1.24 |
| 2001/0025196 A1 | 9/2001 | Chinn et al. |
| 2001/0032013 A1 | 10/2001 | Marton |
| 2001/0039450 A1 | 11/2001 | Pavcnik et al. |
| 2001/0041928 A1 | 11/2001 | Pavcnik et al. |
| 2001/0044647 A1 | 11/2001 | Pinchuk et al. |
| 2002/0010508 A1 | 1/2002 | Chobotov |
| 2002/0029014 A1 | 3/2002 | Jayaraman |
| 2002/0032480 A1 | 3/2002 | Spence et al. |
| 2002/0032481 A1 | 3/2002 | Gabbay |
| 2002/0035396 A1 | 3/2002 | Heath |
| 2002/0042650 A1 | 4/2002 | Vardi et al. |
| 2002/0052651 A1 | 5/2002 | Myers et al. |
| 2002/0058993 A1 | 5/2002 | Landau et al. |
| 2002/0058995 A1 | 5/2002 | Stevens |
| 2002/0072789 A1 | 6/2002 | Hackett et al. |
| 2002/0095209 A1 | 7/2002 | Zadno-Azizi et al. |
| 2002/0099439 A1 | 7/2002 | Schwartz et al. |
| 2002/0103533 A1 | 8/2002 | Langberg et al. |
| 2002/0107565 A1 | 8/2002 | Greenhalgh |
| 2002/0111674 A1 | 8/2002 | Chouinard et al. |
| 2002/0123802 A1 | 9/2002 | Snyders |
| 2002/0133183 A1 | 9/2002 | Lentz et al. |
| 2002/0138138 A1 | 9/2002 | Yang |
| 2002/0151970 A1 | 10/2002 | Garrison et al. |
| 2002/0161392 A1 | 10/2002 | Dubrul |
| 2002/0161394 A1 | 10/2002 | Macoviak et al. |
| 2002/0193871 A1 | 12/2002 | Beyersdorf et al. |
| 2003/0014104 A1 | 1/2003 | Cribier |
| 2003/0023300 A1 | 1/2003 | Bailey et al. |
| 2003/0023303 A1 | 1/2003 | Palmaz et al. |
| 2003/0028247 A1 | 2/2003 | Cali |
| 2003/0026791 A1 | 2/2003 | Bonhoeffer et al. |
| 2003/0036795 A1 | 2/2003 | Andersen et al. |
| 2003/0040771 A1 | 2/2003 | Hyodoh et al. |
| 2003/0040772 A1 | 2/2003 | Hyodoh et al. |
| 2003/0040792 A1 | 2/2003 | Gabbay |
| 2003/0050694 A1 | 3/2003 | Yang et al. |
| 2003/0055495 A1 | 3/2003 | Pease et al. |
| 2003/0065386 A1 | 4/2003 | Weadock |
| 2003/0069492 A1 | 4/2003 | Abrams et al. |
| 2003/0109924 A1 | 6/2003 | Cribier |
| 2003/0125795 A1 | 7/2003 | Pavcnik et al. |
| 2003/0130726 A1 | 7/2003 | Thorpe et al. |
| 2003/0130729 A1 | 7/2003 | Paniagua et al. |
| 2003/0139804 A1 | 7/2003 | Hankh et al. |
| 2003/0149475 A1 | 8/2003 | Hyodoh et al. |
| 2003/0149476 A1 | 8/2003 | Damm et al. |
| 2003/0149478 A1 | 8/2003 | Figulla et al. |
| 2003/0153974 A1 | 8/2003 | Spenser et al. |
| 2003/0181850 A1 | 9/2003 | Diamond et al. |
| 2003/0191519 A1 | 10/2003 | Lombardi et al. |
| 2003/0199913 A1 | 10/2003 | Dubrul et al. |
| 2003/0199963 A1 | 10/2003 | Tower et al. |
| 2003/0199971 A1 | 10/2003 | Tower et al. |
| 2003/0212410 A1 | 11/2003 | Stenzel et al. |
| 2003/0212454 A1 | 11/2003 | Scott et al. |
| 2003/0225445 A1 | 12/2003 | Derus et al. |
| 2004/0019374 A1 | 1/2004 | Hojeibane et al. |
| 2004/0034411 A1 | 2/2004 | Quijano et al. |
| 2004/0039436 A1 | 2/2004 | Spenser et al. |
| 2004/0049211 A1 | 3/2004 | Tremulis et al. |
| 2004/0049224 A1 | 3/2004 | Buehlmann et al. |
| 2004/0049262 A1 | 3/2004 | Obermiller et al. |
| 2004/0049266 A1 | 3/2004 | Anduiza et al. |
| 2004/0082904 A1 | 4/2004 | Houde et al. |
| 2004/0088045 A1 | 5/2004 | Cox |
| 2004/0092858 A1 | 5/2004 | Wilson et al. |
| 2004/0092989 A1 | 5/2004 | Wilson et al. |
| 2004/0093005 A1 | 5/2004 | Durcan |
| 2004/0093060 A1 | 5/2004 | Sequin et al. |
| 2004/0093075 A1 | 5/2004 | Kuehn |
| 2004/0097788 A1 | 5/2004 | Mourles et al. |
| 2004/0098112 A1 | 5/2004 | DiMatteo et al. |
| 2004/0106976 A1 | 6/2004 | Bailey et al. |
| 2004/0106990 A1 | 6/2004 | Spence et al. |
| 2004/0111096 A1 | 6/2004 | Tu et al. |
| 2004/0116951 A1 | 6/2004 | Rosengart |
| 2004/0117004 A1 | 6/2004 | Osborne et al. |
| 2004/0122468 A1 | 6/2004 | Yodfat et al. |
| 2004/0122514 A1 | 6/2004 | Fogarty et al. |
| 2004/0122516 A1 | 6/2004 | Fogarty |
| 2004/0127979 A1 | 7/2004 | Wilson |
| 2004/0138742 A1 | 7/2004 | Myers et al. |
| 2004/0138743 A1 | 7/2004 | Myers et al. |
| 2004/0153146 A1 | 8/2004 | Lashinski et al. |
| 2004/0167573 A1 | 8/2004 | Williamson |
| 2004/0167620 A1 | 8/2004 | Ortiz |
| 2004/0186563 A1 | 9/2004 | Iobbi |
| 2004/0193261 A1 | 9/2004 | Berreklouw |
| 2004/0210240 A1 | 10/2004 | Saint |
| 2004/0210304 A1 | 10/2004 | Seguin et al. |
| 2004/0210307 A1 | 10/2004 | Khairkhahan |
| 2004/0215333 A1 | 10/2004 | Duran |
| 2004/0215339 A1 | 10/2004 | Drasler et al. |
| 2004/0225353 A1 | 11/2004 | McGuckin, Jr. |
| 2004/0225354 A1 | 11/2004 | Allen |
| 2004/0254636 A1 | 12/2004 | Flagle et al. |
| 2004/0260389 A1 | 12/2004 | Case et al. |
| 2004/0260390 A1* | 12/2004 | Sarac .............. A61F 2/2415 623/1.24 |
| 2004/0260394 A1 | 12/2004 | Douk et al. |
| 2004/0267357 A1 | 12/2004 | Allen et al. |
| 2005/0010246 A1 | 1/2005 | Streeter |
| 2005/0010285 A1 | 1/2005 | Lambrecht et al. |
| 2005/0010287 A1 | 1/2005 | Macoviak |
| 2005/0015112 A1 | 1/2005 | Cohn et al. |
| 2005/0027348 A1 | 2/2005 | Case et al. |
| 2005/0033398 A1 | 2/2005 | Seguin |
| 2005/0038509 A1* | 2/2005 | Ashe .............. A61F 2/2454 623/2.36 |
| 2005/0043790 A1 | 2/2005 | Seguin |
| 2005/0049692 A1 | 3/2005 | Numamoto |
| 2005/0049696 A1 | 3/2005 | Siess |
| 2005/0055088 A1 | 3/2005 | Liddicoat et al. |
| 2005/0060029 A1 | 3/2005 | Le |
| 2005/0060030 A1 | 3/2005 | Lashinski et al. |
| 2005/0075584 A1 | 4/2005 | Cali |
| 2005/0075712 A1 | 4/2005 | Biancucci |
| 2005/0075717 A1 | 4/2005 | Nguyen |
| 2005/0075719 A1 | 4/2005 | Bergheim |
| 2005/0075724 A1 | 4/2005 | Svanidze |
| 2005/0075727 A1 | 4/2005 | Wheatley |
| 2005/0075730 A1 | 4/2005 | Myers |
| 2005/0075731 A1 | 4/2005 | Artof |
| 2005/0085841 A1 | 4/2005 | Eversull et al. |
| 2005/0085842 A1 | 4/2005 | Eversull et al. |
| 2005/0085843 A1 | 4/2005 | Opolski et al. |
| 2005/0085890 A1 | 4/2005 | Rasmussen et al. |
| 2005/0085900 A1 | 4/2005 | Case et al. |
| 2005/0096568 A1 | 5/2005 | Kato |
| 2005/0096692 A1 | 5/2005 | Linder et al. |
| 2005/0096724 A1 | 5/2005 | Stenzel et al. |
| 2005/0096734 A1 | 5/2005 | Majercak et al. |
| 2005/0096735 A1 | 5/2005 | Hojeibane et al. |
| 2005/0096736 A1 | 5/2005 | Osse et al. |
| 2005/0096738 A1 | 5/2005 | Cali et al. |
| 2005/0107871 A1 | 5/2005 | Realyvasquez et al. |
| 2005/0113910 A1 | 5/2005 | Paniagua |
| 2005/0119688 A1 | 6/2005 | Berheim |
| 2005/0131438 A1 | 6/2005 | Cohn |
| 2005/0137686 A1 | 6/2005 | Salahieh |
| 2005/0137688 A1 | 6/2005 | Salahieh et al. |
| 2005/0137692 A1 | 6/2005 | Haug |
| 2005/0137695 A1 | 6/2005 | Salahieh |
| 2005/0137701 A1 | 6/2005 | Salahieh |

(56) References Cited

U.S. PATENT DOCUMENTS

| | | |
|---|---|---|
| 2005/0143807 A1 | 6/2005 | Pavcnik et al. |
| 2005/0143809 A1 | 6/2005 | Salahieh |
| 2005/0148997 A1 | 7/2005 | Valley et al. |
| 2005/0149181 A1 | 7/2005 | Eberhardt |
| 2005/0165477 A1 | 7/2005 | Anduiza et al. |
| 2005/0187616 A1 | 8/2005 | Realyvasquez |
| 2005/0197695 A1 | 9/2005 | Stacchino et al. |
| 2005/0203549 A1 | 9/2005 | Realyvasquez |
| 2005/0203605 A1 | 9/2005 | Dolan |
| 2005/0203618 A1 | 9/2005 | Sharkawy |
| 2005/0222674 A1 | 10/2005 | Paine |
| 2005/0228495 A1 | 10/2005 | Macoviak |
| 2005/0234546 A1 | 10/2005 | Nugent |
| 2005/0240200 A1 | 10/2005 | Bergheim |
| 2005/0240263 A1 | 10/2005 | Fogarty et al. |
| 2005/0261759 A1 | 11/2005 | Lambrecht et al. |
| 2005/0283962 A1 | 12/2005 | Boudjemline |
| 2006/0004439 A1 | 1/2006 | Spenser et al. |
| 2006/0004469 A1 | 1/2006 | Sokel |
| 2006/0009841 A1 | 1/2006 | McGuckin et al. |
| 2006/0020327 A1* | 1/2006 | Lashinski .......... A61B 17/0644 623/1.25 |
| 2006/0030885 A1 | 2/2006 | Hyde |
| 2006/0052867 A1 | 3/2006 | Revuelta et al. |
| 2006/0058775 A1 | 3/2006 | Stevens et al. |
| 2006/0089711 A1 | 4/2006 | Dolan |
| 2006/0100685 A1 | 5/2006 | Seguin et al. |
| 2006/0116757 A1 | 6/2006 | Lashinski et al. |
| 2006/0135964 A1 | 6/2006 | Vesely |
| 2006/0142848 A1 | 6/2006 | Gabbay |
| 2006/0167474 A1 | 7/2006 | Bloom et al. |
| 2006/0178740 A1 | 8/2006 | Stacchino et al. |
| 2006/0195134 A1 | 8/2006 | Crittenden |
| 2006/0195183 A1* | 8/2006 | Navia .................. A61F 2/2409 623/2.18 |
| 2006/0206192 A1 | 9/2006 | Tower et al. |
| 2006/0206202 A1 | 9/2006 | Bonhoefer et al. |
| 2006/0212111 A1 | 9/2006 | Case et al. |
| 2006/0247763 A1 | 11/2006 | Slater |
| 2006/0259134 A1 | 11/2006 | Schwammenthal et al. |
| 2006/0259136 A1 | 11/2006 | Nguyen et al. |
| 2006/0259137 A1 | 11/2006 | Artof et al. |
| 2006/0265056 A1 | 11/2006 | Nguyen et al. |
| 2006/0271166 A1 | 11/2006 | Thill et al. |
| 2006/0271175 A1 | 11/2006 | Woolfson et al. |
| 2006/0276874 A1 | 12/2006 | Wilson et al. |
| 2006/0276882 A1 | 12/2006 | Case et al. |
| 2006/0282161 A1 | 12/2006 | Huynh et al. |
| 2007/0005129 A1 | 1/2007 | Damm et al. |
| 2007/0005131 A1 | 1/2007 | Taylor |
| 2007/0010878 A1 | 1/2007 | Raffiee et al. |
| 2007/0016286 A1 | 1/2007 | Case et al. |
| 2007/0027518 A1 | 2/2007 | Herrmann et al. |
| 2007/0027533 A1 | 2/2007 | Douk |
| 2007/0038295 A1 | 2/2007 | Case et al. |
| 2007/0043431 A1 | 2/2007 | Melsheimer |
| 2007/0043435 A1 | 2/2007 | Seguin et al. |
| 2007/0051377 A1 | 3/2007 | Douk et al. |
| 2007/0073392 A1 | 3/2007 | Heyninck-Janitz |
| 2007/0078509 A1 | 4/2007 | Lotfy et al. |
| 2007/0078510 A1 | 4/2007 | Ryan |
| 2007/0088431 A1 | 4/2007 | Bourang et al. |
| 2007/0093869 A1 | 4/2007 | Bloom et al. |
| 2007/0100439 A1 | 5/2007 | Cangialosi |
| 2007/0100440 A1 | 5/2007 | Figulla |
| 2007/0100449 A1 | 5/2007 | O'Neil et al. |
| 2007/0112415 A1 | 5/2007 | Bartlett |
| 2007/0112422 A1 | 5/2007 | Dehdashtian |
| 2007/0156233 A1* | 7/2007 | Kapadia ................ A61F 2/2409 623/2.11 |
| 2007/0162102 A1 | 7/2007 | Ryan et al. |
| 2007/0162113 A1 | 7/2007 | Sharkawy et al. |
| 2007/0185513 A1 | 8/2007 | Woolfson et al. |
| 2007/0203391 A1 | 8/2007 | Bloom et al. |
| 2007/0225681 A1 | 9/2007 | House |
| 2007/0232898 A1 | 10/2007 | Huynh et al. |
| 2007/0233228 A1 | 10/2007 | Eberhardt et al. |
| 2007/0233237 A1 | 10/2007 | Krivoruchko |
| 2007/0233238 A1 | 10/2007 | Huynh et al. |
| 2007/0238979 A1 | 10/2007 | Huynh et al. |
| 2007/0239254 A1 | 10/2007 | Marchand et al. |
| 2007/0239265 A1 | 10/2007 | Birdsall |
| 2007/0239266 A1 | 10/2007 | Birdsall |
| 2007/0239269 A1 | 10/2007 | Dolan et al. |
| 2007/0239271 A1 | 10/2007 | Nguyen |
| 2007/0239273 A1 | 10/2007 | Allen |
| 2007/0244544 A1 | 10/2007 | Birdsall et al. |
| 2007/0244545 A1 | 10/2007 | Birdsall et al. |
| 2007/0244546 A1 | 10/2007 | Francis |
| 2007/0244553 A1 | 10/2007 | Rafiee et al. |
| 2007/0244554 A1 | 10/2007 | Rafiee et al. |
| 2007/0244555 A1 | 10/2007 | Rafiee et al. |
| 2007/0244556 A1 | 10/2007 | Rafiee et al. |
| 2007/0244557 A1 | 10/2007 | Rafiee et al. |
| 2007/0250160 A1 | 10/2007 | Rafiee |
| 2007/0255394 A1 | 11/2007 | Ryan |
| 2007/0255396 A1 | 11/2007 | Douk et al. |
| 2007/0288000 A1 | 12/2007 | Bonan |
| 2008/0004696 A1 | 1/2008 | Vesely |
| 2008/0009940 A1 | 1/2008 | Cribier |
| 2008/0015671 A1 | 1/2008 | Bonhoeffer |
| 2008/0021552 A1 | 1/2008 | Gabbay |
| 2008/0048656 A1 | 2/2008 | Tan |
| 2008/0065001 A1 | 3/2008 | Marchand et al. |
| 2008/0065206 A1 | 3/2008 | Liddicoat |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0077234 A1 | 3/2008 | Styrc |
| 2008/0082165 A1 | 4/2008 | Wilson et al. |
| 2008/0082166 A1 | 4/2008 | Styrc et al. |
| 2008/0133003 A1 | 6/2008 | Seguin et al. |
| 2008/0140189 A1 | 6/2008 | Nguyen et al. |
| 2008/0147105 A1 | 6/2008 | Wilson et al. |
| 2008/0147180 A1 | 6/2008 | Ghione et al. |
| 2008/0147181 A1 | 6/2008 | Ghione et al. |
| 2008/0147182 A1 | 6/2008 | Righini et al. |
| 2008/0154355 A1 | 6/2008 | Benichow et al. |
| 2008/0154356 A1 | 6/2008 | Obermiller et al. |
| 2008/0161910 A1 | 7/2008 | Revuelta et al. |
| 2008/0161911 A1 | 7/2008 | Revuelta et al. |
| 2008/0183273 A1* | 7/2008 | Mesana ................ A61F 2/2418 623/1.11 |
| 2008/0188928 A1 | 8/2008 | Salahieh et al. |
| 2008/0215143 A1 | 9/2008 | Seguin et al. |
| 2008/0215144 A1 | 9/2008 | Ryan et al. |
| 2008/0228254 A1 | 9/2008 | Ryan |
| 2008/0228263 A1 | 9/2008 | Ryan |
| 2008/0234797 A1 | 9/2008 | Styrc |
| 2008/0243246 A1 | 10/2008 | Ryan et al. |
| 2008/0255651 A1 | 10/2008 | Dwork |
| 2008/0255660 A1 | 10/2008 | Guyenot et al. |
| 2008/0255661 A1 | 10/2008 | Straubinger et al. |
| 2008/0262593 A1 | 10/2008 | Ryan et al. |
| 2008/0269878 A1 | 10/2008 | Iobbi |
| 2009/0005863 A1 | 1/2009 | Goetz et al. |
| 2009/0012600 A1 | 1/2009 | Styrc et al. |
| 2009/0048656 A1 | 2/2009 | Wen |
| 2009/0054976 A1 | 2/2009 | Tuval et al. |
| 2009/0069886 A1 | 3/2009 | Suri et al. |
| 2009/0069887 A1 | 3/2009 | Righini et al. |
| 2009/0069889 A1 | 3/2009 | Suri et al. |
| 2009/0082858 A1 | 3/2009 | Nugent et al. |
| 2009/0085900 A1 | 4/2009 | Weiner |
| 2009/0099653 A1 | 4/2009 | Suri et al. |
| 2009/0138079 A1 | 5/2009 | Tuval et al. |
| 2009/0164004 A1 | 6/2009 | Cohn |
| 2009/0164006 A1 | 6/2009 | Seguin et al. |
| 2009/0171447 A1 | 7/2009 | VonSeggesser et al. |
| 2009/0192585 A1 | 7/2009 | Bloom et al. |
| 2009/0192586 A1 | 7/2009 | Tabor et al. |
| 2009/0192591 A1 | 7/2009 | Ryan et al. |

(56) References Cited

U.S. PATENT DOCUMENTS

| | | | |
|---|---|---|---|
| 2009/0198316 A1 | 8/2009 | Laske et al. |
| 2009/0216310 A1 | 8/2009 | Straubinger et al. |
| 2009/0216312 A1 | 8/2009 | Straubinger et al. |
| 2009/0216313 A1 | 8/2009 | Straubinger et al. |
| 2009/0222082 A1 | 9/2009 | Lock et al. |
| 2009/0234443 A1 | 9/2009 | Ottma et al. |
| 2009/0240264 A1 | 9/2009 | Tuval et al. |
| 2009/0240320 A1 | 9/2009 | Tuval |
| 2009/0287296 A1 | 11/2009 | Manasse |
| 2010/0004740 A1 | 1/2010 | Seguin et al. |
| 2010/0030328 A1 | 2/2010 | Seguin et al. |
| 2010/0036479 A1 | 2/2010 | Hill et al. |
| 2010/0036485 A1 | 2/2010 | Seguin |
| 2010/0069852 A1 | 3/2010 | Kelley |
| 2010/0094411 A1 | 4/2010 | Tuval et al. |
| 2010/0100167 A1 | 4/2010 | Bortlein et al. |
| 2010/0131054 A1 | 5/2010 | Tuval et al. |
| 2010/0137979 A1 | 6/2010 | Tuval et al. |
| 2010/0145439 A1 | 6/2010 | Seguin et al. |
| 2010/0152840 A1 | 6/2010 | Seguin et al. |
| 2010/0161045 A1 | 6/2010 | Righini |
| 2010/0198346 A1 | 8/2010 | Keogh et al. |
| 2010/0234940 A1 | 9/2010 | Dolan |
| 2010/0256723 A1 | 10/2010 | Murray |

FOREIGN PATENT DOCUMENTS

| | | |
|---|---|---|
| DE | 195 32 846 | 3/1997 |
| DE | 195 46 692 A1 | 6/1997 |
| DE | 195 46 692 C2 | 6/1997 |
| DE | 198 57 887 A1 | 7/2000 |
| DE | 199 07 646 | 8/2000 |
| DE | 100 10 074 | 10/2001 |
| DE | 100 49 812 | 4/2002 |
| DE | 100 49 813 | 4/2002 |
| DE | 100 49 815 | 4/2002 |
| EP | 1057460 A1 | 6/2000 |
| EP | 1255510 | 11/2002 |
| EP | 1469797 | 11/2005 |
| FR | 2788217 | 12/1999 |
| FR | 2815844 | 5/2000 |
| GB | 2056023 | 3/1981 |
| GB | 2433700 | 12/2007 |
| SU | 1271508 | 11/1986 |
| WO | 95/29640 | 11/1995 |
| WO | 00/44313 | 8/2000 |
| WO | 00/47136 | 8/2000 |
| WO | 01/35870 | 5/2001 |
| WO | 01/49213 | 7/2001 |
| WO | 01/54625 | 8/2001 |
| WO | 01/62189 | 8/2001 |
| WO | 01/64137 | 9/2001 |
| WO | 02/03892 | 1/2002 |
| WO | 02/22054 | 3/2002 |
| WO | 02/36048 | 5/2002 |
| WO | 03/003943 | 1/2003 |
| WO | 03/003949 | 1/2003 |
| WO | 03/011195 | 2/2003 |
| WO | 04/019825 | 3/2004 |
| WO | 04/089250 | 10/2004 |
| WO | 04/103223 | 12/2004 |
| WO | 05/004753 | 1/2005 |
| WO | 05/046528 | 5/2005 |
| WO | 05/087139 | 9/2005 |
| WO | 06/026371 | 3/2006 |
| WO | 06/091163 | 8/2006 |
| WO | 08/047354 | 4/2008 |
| WO | 08/138584 | 11/2008 |
| WO | 08/150529 | 12/2008 |
| WO | 09/002548 | 12/2008 |
| WO | 09/029199 | 3/2009 |
| WO | 09/042196 | 4/2009 |
| WO | 09/045338 | 4/2009 |
| WO | 09/061389 | 5/2009 |
| WO | 09/091509 | 7/2009 |
| WO | 09/111241 | 9/2009 |

OTHER PUBLICATIONS

Babaliaros, et al., "State of the Art Percutaneous Intervention for the Treatment of Valvular Heart Disease: A Review of the Current Technologies and Ongoing Research in the Field of Percutaneous Heart Valve Replacement and Repair," Cardiology 2007; 107:87-96.

Bailey, "Percutaneous Expandable Prosthetic Valves," In: Topol EJ, ed. Textbook of Interventional Cardiology. vol. II. Second edition. WB Saunders, Philadelphia, 1994:1268-1276.

Block, et al., "Percutaneous Approaches to Valvular Heart Disease," Current Cardiology Reports, vol. 7 (2005) pp. 108-113.

Bonhoeffer, et al, "Percutaneous Insertion of the Pulmonary Valve," Journal of the American College of Cardiology (United States), May 15, 2002, pp. 1664-1669.

Bonhoeffer, et al, "Percutaneous Replacement of Pulmonary Valve in a Right-Ventricle to Pulmonary-Artery Prosthetic Conduit with Valve Dysfunction," Lancet (England), Oct. 21, 2000, pp. 1403-1405.

Bonhoeffer, et al, "Transcatheter Implantation of a Bovine Valve in Pulmonary Position: A Lamb Study," Circulation (United States), Aug. 15, 2000, pp. 813-816.

Boudjemline, et al, "Images in Cardiovascular Medicine. Percutaneous Aortic Valve Replacement in Animals," Circulation (United States), Mar. 16, 2004, 109, p. e161.

Boudjemline, et al, "Is Percutaneous Implantation of a Bovine Venous Valve in the Inferior Vena Cava a Reliable Technique to Treat Chronic Venous Insufficiency Syndrome?" Medical Science Monitor—International Medical Journal of Experimental and Clinical Research (Poland), Mar. 2004, pp. BR61-BR66.

Boudjemline, et al, "Off-pump Replacement of the Pulmonary Valve in Large Right Ventricular Outflow Tracts: A Hybrid Approach," Journal of Thoracic and Cardiovascular Surgery (United States), Apr. 2005, pp. 831-837.

Boudjemline, et al, "Percutaneous Aortic Valve Replacement: Will We Get There?" Heart (British Cardiac Society) (England), Dec. 2001, pp. 705-706.

Boudjemline, et al, "Percutaneous Implantation of a Biological Valve in the Aorta to Treat Aortic Valve Insufficiency—A Sheep Study," Medical Science Monitor—International Medical Journal of Experimental and Clinical Research (Poland), Apr. 2002, pp. BR113-BR116.

Boudjemline, et al, "Percutaneous Implantation of a Biological Valve in Aortic Position: Preliminary Results in a Sheep Study," European Heart Journal 22, Sep. 2001, p. 630.

Boudjemline, et al, "Percutaneous Implantation of a Valve in the Descending Aorta in Lambs," European Heart Journal (England), Jul. 2002, pp. 1045-1049.

Boudjemline, et al, "Percutaneous Pulmonary Valve Replacement in a Large Right Ventricular Outflow Tract: An Experimental Study," Journal of the American College of Cardiology (United States), Mar. 17, 2004, pp. 1082-1087.

Boudjemline, et al, "Percutaneous Valve Insertion: A New Approach," Journal of Thoracic and Cardiovascular Surgery (United States), Mar. 2003, pp. 741-742.

Boudjemline, et al, "Stent Implantation Combined with a Valve Replacement to Treat Degenerated Right Ventricle to Pulmonary Artery Prosthetic Conduits," European Heart Journal 22, Sep. 2001, p. 355.

Boudjemline, et al, "Steps Toward Percutaneous Aortic Valve Replacement," Circulation (United States), Feb. 12, 2002, pp. 775-778.

Boudjemline, et al, "The Percutaneous Implantable Heart Valve," Progress in Pediatric Cardiology (Ireland), 2001, pp. 89-93.

Boudjemline, et al, "Transcatheter Reconstruction of the Right Heart," Cardiology in the Young (England), Jun. 2003, pp. 308-311.

(56) References Cited

OTHER PUBLICATIONS

Coats, et al, "The Potential Impact of Percutaneous Pulmonary Valve Stent Implantation on Right Ventricular Outflow Tract Re-Intervention," European Journal of Cardio-Thoracic Surgery (England), Apr. 2005, pp. 536-543.

Cribier, A. et al, "Percutaneous Transcatheter Implantation of an Aortic Valve Prosthesis for Calcific Aortic Stenosis: First Human Case Description," Circulation (2002) 3006-3008.

Davidson et al., "Percutaneous therapies for valvular heart disease," Cardiovascular Pathology 15 (2006) 123-129.

Hanzel, et al., "Complications of percutaneous aortic valve replacement: experience with the Criber-Edwards™ percutaneous heart valve," EuroIntervention Supplements (2006), 1 (Supplement A) A3-A8.

Huber, et al., "Do Valved Stents Compromise Coronary Flow?" Eur. J. Cardiothorac. Surg. 2004;25:754-759.

Khambadkone, "Nonsurgical Pulmonary Valve Replacement: Why, When, and How?" Catheterization and Cardiovascular Interventions—Official Journal of the Society for Cardiac Angiography & Interventions (United States), Jul. 2004, pp. 401-408.

Khambadkone, et al, "Percutaneous Implantation of Pulmonary Valves," Expert Review of Cardiovascular Therapy (England), Nov. 2003, pp. 541-548.

Khambadkone, et al, "Percutaneous Pulmonary Valve Implantation: Early and Medium Term Results," Circulation 108 (17 Supplement), Oct. 28, 2003, p. IV-375.

Khambadkone, et al, "Percutaneous Pulmonary Valve Implantation: Impact of Morphology on Case Selection," Circulation 108 (17 Supplement), Oct. 28, 2003, p. IV-642-IV-643.

Lutter, et al, "Percutaneous Aortic Valve Replacement: An Experimental Study. I. Studies on Implantation," The Journal of Thoracic and Cardiovascular Surgery, Apr. 2002, pp. 768-776.

Lutter, et al, "Percutaneous Valve Replacement: Current State and Future Prospects," Annals of Thoracic Surgery (Netherlands), Dec. 2004, pp. 2199-2206.

Ma, Ling, et al., "Double-crowned valved stents for off-pump mitral valve replacement," European Journal of Cardio Thoracic Surgery, 28:194-198, 2005.

Medtech Insight, "New Frontiers in Heart Valve Disease," vol. 7, No. 8 (2005).

Palacios, "Percutaneous Valve Replacement and Repair, Fiction or Reality?" Journal of American College of Cardiology, vol. 44, No. 8 (2004) pp. 1662-1663.

Pelton et al., "Medical Uses of Nitinol," Materials Science Forum vols. 327-328, pp. 63-70 (2000).

Ruiz, "Transcathether Aortic Valve Implantation and Mitral Valve Repair: State of the Art," Pediatric Cardiology, vol. 26, No. 3 (2005).

Saliba, et al, "Treatment of Obstructions of Prosthetic Conduits by Percutaneous Implantation of Stents," Archives des Maldies du Coeur et des Vaisseaux (France), 1999, pp. 591-596.

Webb, et al., "Percutaneous Aortic Valve Implantation Retrograde from the Femoral Artery," Circulation (2006), 113;842-850.

Stassano et al., "Mid-term results of the valve-on-valve technique for bioprosthetic failure," Eur. J. Cardiothorac. Surg. 2000; 18:453-457.

Pavcnik et al., "Aortic and venous valve for percutaneous insertion," Min. Invas. Ther. & Allied Techol. 2000, vol. 9, pp. 287-292.

* cited by examiner

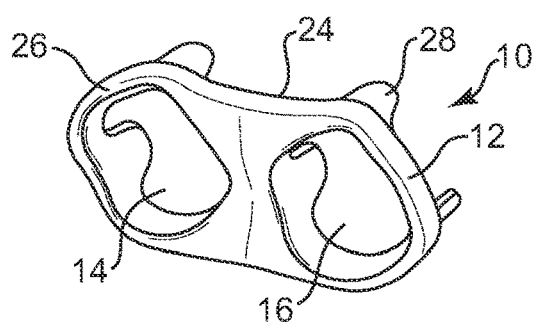
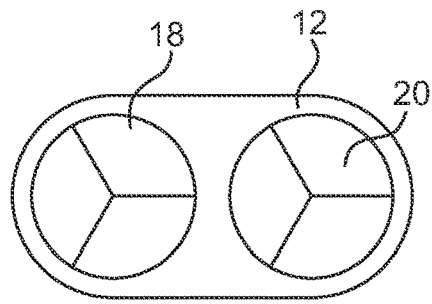
Fig. 1         Fig. 2
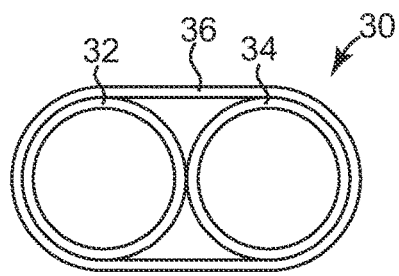
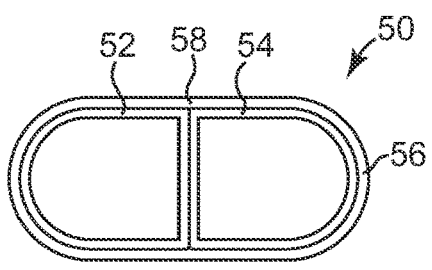
Fig. 3         Fig. 4
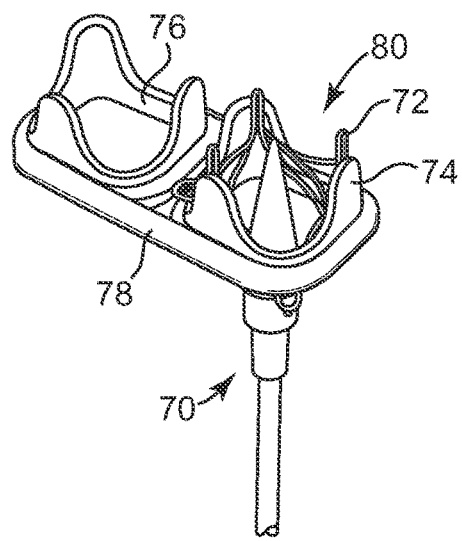
Fig. 5

MULTIPLE ORIFICE IMPLANTABLE HEART VALVE AND METHODS OF IMPLANTATION

CROSS-REFERENCE TO RELATED APPLICATION

The present application is a Continuation of and claims priority to U.S. patent application Ser. No. 13/860,779, filed Apr. 11, 2013; which is a Continuation of U.S. patent application Ser. No. 12/364,246, filed Feb. 2, 2009, now U.S. Pat. No. 8,430,927, which claims priority to U.S. Provisional Application No. 61/123,337, filed Apr. 8, 2008, and titled "Double Orifice Implantable Heart Valve", the entire contents of which is incorporated herein by reference in its entirety.

TECHNICAL FIELD

The present invention relates generally to devices and methods for repair of heart valves, and more particularly to prosthetic heart valves for use in replacement of the mitral valve.

BACKGROUND

One of the two atrio-ventricular valves in the heart is the mitral valve, which is located on the left side of the heart and which forms or defines a valve annulus and valve leaflets. The mitral valve is located between the left atrium and the left ventricle, and serves to direct oxygenated blood from the lungs through the left side of the heart and into the aorta for distribution to the body. As with other valves of the heart, the mitral valve is a passive structure in that it does not itself expend any energy and does not perform any active contractile function.

The mitral valve includes two moveable leaflets that open and close in response to differential pressures on either side of the valve. Ideally, the leaflets move apart from each other when the valve is in an open position, and meet or "coapt" when the valve is in a closed position. However, problems can develop with valves, which can generally be classified as either stenosis, in which a valve does not open properly, or insufficiency (also called regurgitation), in which a valve does not close properly. Stenosis and insufficiency may occur concomitantly in the same valve. The effects of valvular dysfunction vary, with mitral regurgitation or backflow typically having relatively severe physiological consequences to the patient. Regurgitation, along with other abnormalities of the mitral valve, can increase the workload placed on the heart. The severity of this increased stress on the heart and the patient, and the ability of the heart to adapt to it, determine the treatment options that are available for a particular patient. In some cases, medication can be sufficient to treat the patient, which is the preferred option when it is viable; however, in many cases, defective valves have to be repaired or completely replaced in order to adequately restore the function of the heart.

One situation where repair of a mitral valve is often viable is when the defects present in the valve are associated with dilation of the valve annulus, which not only prevents competence of the valve but also results in distortion of the normal shape of the valve orifice. Remodeling of the annulus is central to these types of reconstructive procedures on the mitral valve. When a mitral valve is repaired, the result is generally a reduction in the size of the posterior segment of the mitral valve annulus. As a part of the mitral valve repair, the involved segment of the annulus is diminished (i.e., constricted) so that the leaflets may coapt correctly on closing, and/or the annulus is stabilized to prevent post-operative dilatation from occurring. Either result is frequently achieved by the implantation of a prosthetic ring or band in the supra annular position. The purpose of the ring or band is to restrict, remodel and/or support the annulus to correct and/or prevent valvular insufficiency. Such repairs of the valve, when technically possible, can produce relatively good long-term results.

However, valve repair is sometimes either impossible, undesirable, or has failed, such as in cases where the problem is not related to dilation of the valve annulus, leaving valve replacement as the most viable option for improving operation of the mitral valve. The two general categories of valves that are used for mitral valve replacement are mechanical valves and bioprosthetic or tissue valves. A wide variety of mechanical valves are available that accommodate the blood flow requirements of the particular location where they will be implanted; however, the use of these mechanical devices in the body can increase the risk of clotting in the blood stream, which can lead to a heart attack or stroke. Thus, mechanical valve recipients must take anti-coagulant drugs for the rest of their lives to minimize the potential of blood clots. The use of tissue valves advantageously eliminates the need for such anti-coagulant drugs; however, tissue valves do not typically last as long as mechanical valves and may need to be replaced at some later point in the patient's life. To implant either mechanical or tissue valves, a surgical procedure is typically used that involves opening the patient's chest to access the mitral valve through the left atrium, and then implanting the new valve in position.

To simplify surgical procedures and reduce patient trauma, there has been a recent increased interest in minimally invasive and percutaneous replacement of cardiac valves. Such a replacement of a heart valve typically does not involve actual physical removal of the diseased or injured native heart valve, but instead includes delivery of a replacement valve in a compressed condition to the native valve site, where it is expanded. One example of such a replacement procedure for a pulmonary valve includes inserting a replacement pulmonary valve into a balloon catheter and delivering it percutaneously via the vascular system to the location of a failed pulmonary valve. There, the replacement valve is expanded by a balloon to compress the native valve leaflets against the right ventricular outflow tract, thereby anchoring and sealing the replacement valve. In the context of percutaneous pulmonary valve replacement, U.S. Patent Application Publication Nos. 2003/0199971 A1 and 2003/0199963 A1, both filed by Tower, et al., describe a valved segment of bovine jugular vein, mounted within an expandable stent, for use as a replacement pulmonary valve. As described in the articles: "Percutaneous Insertion of the Pulmonary Valve", Bonhoeffer, et al., Journal of the American College of Cardiology 2002; 39: 1664-1669 and "Transcatheter Replacement of a Bovine Valve in Pulmonary Position", Bonhoeffer, et al., Circulation 2000; 102: 813-816, a replacement pulmonary valve may be implanted to replace native pulmonary valves or prosthetic pulmonary valves located in valved conduits. Other implantables and implant delivery devices also are disclosed in published U.S. Patent Application Publication No. 2003/0036791 A1 and European Patent Application No. 1 057 460-A1.

The percutaneous valve implantation procedures described above typically involve the movement of a compressed valve through at least some portion of the vasculature of the patient to the delivery site, and are therefore particularly well-suited for implanting relatively small valves, such pulmonary valves or aortic valves. Because a replacement mitral valve is typically relatively large as compared to the portions of the anatomy through which it would need to travel to reach the region of the native mitral valve, the percutaneous valve implantation procedures described in the above journal articles may not be feasible for a mitral valve. However, there is a continued desire to be able to be able to improve mitral valve replacement devices and procedures to accommodate the physical structure of the heart without causing undue stress to the patient during the operation on the heart, such as providing devices and methods for replacing the mitral valve percutaneously.

SUMMARY

One embodiment of the invention is a surgically implantable multiple orifice heart valve having a valve frame with at least two orifices, each of which can accommodate a tissue valve. The outer peripheral shape of the valve frame can be modeled for implantation in the mitral valve position, and can therefore be generally circular, oval, or elliptical in shape, with at least two adjacent orifices or openings. The orifices in one embodiment are generally circular in shape, although they can have a different shape than circular, if desired. Each of the orifices within a single valve frame may have the same size and shape as each of the other orifices of that valve frame, or the orifices within a single valve frame can each have a different size and/or shape than the other orifices of that frame in order to adapt to the size and shape of the native valve opening.

A bi-leaflet valve, tri-leaflet valve, or differently configured valve can be mounted within each opening. Each of the individual valves are designed for generally simultaneous opening and closing of the multiple valves that are mounted in the same valve frame. That is, regardless of the leaflet structure provided, each of the heart valves should be oriented and designed so that all of the valves within a single valve frame can open and close at generally the same time within the heart cycle in response to changes in blood flow. In this way, the multiple valves function in generally the same manner as the native valve or as a single replacement valve in the patient. In particular, when the leaflets of both valves are in an open position, an internal passage is defined by each orifice through which blood can flow, and when the leaflets of both valves are in a closed position, the internal passages through the orifices do not allow for the flow of blood through the valves. With specific reference to the mitral valve, the leaflets of the valves of the multiple orifice heart valve will generally function in such a way that blood flows toward the left ventricle when the leaflets are in an open position, and so that blood is prevented from moving toward the left atrium when the leaflets are in a closed position.

It is also within the scope of the invention that the two or more orifices of a valve configuration used in a single valve opening in a patient can be independent such that they can move at least slightly relative to each other. That is, two or more separate orifice structures can be implanted into a single valve space in such a way that movement of the orifice structures relative to each other may be possible during and after implantation.

If a tri-leaflet valve is attached within any of the orifices, three commissure posts can extend from one side of the valve frame and be spaced from each other around each of the orifices. The commissure posts define the juncture between adjacent tissue and/or synthetic leaflets secured to the valve frame. Similar or different structures can be provided to extend from or otherwise be attached to the valve frame for other valve configurations (e.g. for bi-leaflet valves). In some embodiments, it is possible for one or more commissure posts to be shared by adjacent valve structures.

The valve frame is the structure of the multiple orifice heart valve that provides a means of fixing the prosthetic heart valve to the patient's native heart valve orifice tissue (e.g, native annulus or valvular rim) that is associated with the native heart valve being repaired or replaced. The valve frame includes a base portion around or over which a suture material (e.g., a cloth-like material) is disposed for suturing the prosthesis to heart tissue. The suture or cloth-like material portion may also cover any support structures, such as the commissure posts described above.

It is contemplated that the valve frames of the invention are initially implanted without any attached valve structures. The valves can subsequently be delivered in a minimally invasive manner to the orifices in the valve frame and attached via coalescent clips or other means.

Once the valve frame with attached valve structures (e.g., the prosthetic heart valve with multiple orifices, as described above) is implanted within the patient, the valve can be expected to function without problems for a period of time, and possibly as long as several years, without any noticeable issues. However, if deficiencies occur at any time after implantation in one or more of the valves of the multiple-valve structure, each deficient valve can potentially be replaced by percutaneously delivering a new valve via transcatheter implantation. Each of these individual valves would be relatively small as compared to the overall valve size that would be required for percutaneous implantation of a comparable mitral valve that fills the mitral valve space. In this way, the complications and risks involved with additional surgical intervention can be minimized or avoided. Another advantage of using multiple valves with a smaller size instead of one larger diameter valve is that the protrusions or other extending structures of the stent frame can be somewhat smaller. Thus, the protrusions will not extend as far into the ventricle when the device is implanted, thereby reducing the potential for obstruction or damage to the ventricle and/or the native valvular apparatus, such as chordae or papillary muscles.

The invention further includes a method of surgically implanting a multiple orifice valve assembly into the mitral valve area of a patient, then percutaneously delivering a replacement valve, such as a stented valve, to at least one of the orifices of the surgically implanted valve assembly. Each percutaneously delivered replacement valve can include features for proper orientation and positioning relative to the orifice of the surgically implanted heart valve. For one example, the percutaneously delivered valve can include a stent having docking features that are designed or selected to cooperate with features of the valve frame for secure anchoring of the elements relative to each other. Thus, it is within the scope of the invention for the valve frame of the multiple orifice valve assembly to have specific features or elements that allow for a certain type of engagement with a replacement valve having corresponding features. In that regard, the multiple orifice valve assembly and replacement valves can be provided as a kit. With any of the embodiments described above, the valve frames, stents, and other corresponding elements should be provided so that there is minimal interference with the functioning of an adjacent aortic valve. In addition, while many of the embodiments are shown and described as having two orifices in a valve frame, it is understood that the valve frames may include three or more orifices, which can help to accommodate the anatomies of patients having particularly large mitral openings.

BRIEF DESCRIPTION OF THE DRAWINGS

The present invention will be further explained with reference to the appended Figures, wherein like structure is referred to by like numerals throughout the several views, and wherein:

FIG. 1 is a bottom perspective view of one embodiment of a valve frame in accordance with the invention;

FIG. 2 is a top plan view of the valve frame of FIG. 1 and illustrating exemplary valve leaflets in their closed positions;

FIG. 3 is a top plan view of another embodiment of a multiple-orifice valve assembly of the invention;

FIG. 4 is a top plan view of another embodiment of a multiple-orifice valve assembly of the invention;

FIG. 5 is a perspective view of a distal portion of a delivery system positioned relative to one orifice of a portion of a mitral valve replacement assembly;

DETAILED DESCRIPTION

Figure 6:
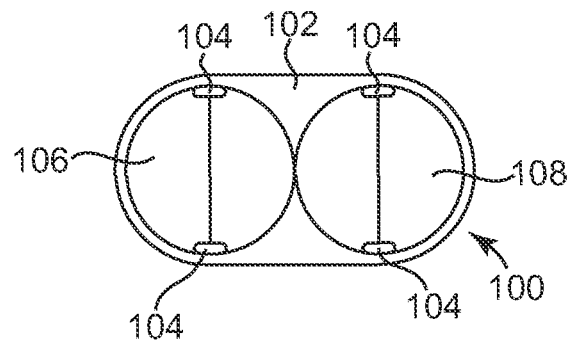
FIG. 6 is a top schematic plan view of another embodiment of a multiple-orifice valve assembly of the invention.

Referring now to the Figures, wherein the components are labeled with like numerals throughout the several Figures, and initially to FIGS. 1 and 2, one embodiment of a double orifice implantable heart valve 10 in accordance with the invention is illustrated. Although the heart valves of the invention, such as heart valve 10, are generally described herein as being used for mitral valve replacement, it is understood that many of the features of these heart valves can be used for valves in other areas of the heart. For example, the heart valves of the invention can be used in any area of the heart where it would be more advantageous to use multiple valves that are relatively small than to use a single valve that is relatively large. In any case, the heart valves of the invention desirably restore normal functioning of a cardiac valve, and are initially implanted using surgical techniques that include minimally invasive methods or more traditional open-heart surgical methods. Further, as used throughout this specification, a "prosthetic heart valve" or "heart valve" is intended to encompass bioprosthetic heart valves having leaflets made of biological material (e.g., harvested porcine valve leaflets, or bovine or equine pericardial leaflets), along with synthetic leaflet materials or other materials.

Heart valve 10 includes a valve frame 12 having a first orifice 14 and a second orifice 16. These orifices 14, 16 are illustrated to be generally the same size and shape as each other, and preferably are sized for attachment of a tissue valve within each of their interior portions. FIG. 2 illustrates the valve frame 12 with a first tri-leaflet valve 18 in its closed position within the first orifice 14 and a second tri-leaflet valve 20 in its closed position within the second orifice 16. This three-leaflet arrangement of valves 18, 20 is exemplary; alternative configurations include a bi-leaflet valve positioned in both of the orifices, and valves that are different from each other in each of the orifices (e.g., one of the orifices includes a three-leaflet valve while the other orifice includes a bi-leaflet valve). In any case, the multi-orifice valve configurations of the invention advantageously allow for replacement of only one of the valves if only one of the valves fails at some point after implantation (while at least one properly functioning valve remains operational), as will be described in further detail below. If such a valve replacement is performed, the specific rotational orientation of the valve leaflets within the orifice may or may not be a consideration.

Referring again to FIG. 1, the valve frame 12 has an outer periphery that is generally oval or elliptical in shape and has a first side 24 and an opposite second side 26. The valve frame 12 is generally shaped or modeled to match the valve space into which it will be surgically implanted. For example, if the valve frame 12 will be placed in the mitral valve space of a patient, characteristics of the specific mitral valve space into which it will be positioned can be taken into account. Thus, the valve frame 12 may have a generally planar surface on its first and second sides 24, 26, or it may have contours and shaping on one or both sides to match the anatomy of the patient. For example, it may be relatively saddle shaped. The valve frame 12 provides a means for fixing the double orifice implantable heart valve 10 to the patient's native heart valve orifice tissue (e.g., the native annulus or valvular rim) that is associated with the native heart valve being repaired or replaced. In particular, a surgical implantation technique can be employed whereby the heart is stopped (e.g., with the use of cardiopulmonary bypass) and opened, which is followed by optional surgical removal of damaged or diseased natural valve structure. The heart valve 10 can then be oriented within the native valvular area, with the valve frame 12 being seated against or at the native annulus or valvular rim. Sutures can then be used to affix the valve frame 12 to the natural tissue.

With the various multiple valve assemblies of the invention, it is desirable to maximize the overall area of the orifices relative to the frame size in order to minimize the obstruction to blood flow. Thus, it is preferable that the sizes of the structural components of the stent frame are minimized, while the desired structural strength of the frame is maintained.

Figure 9:
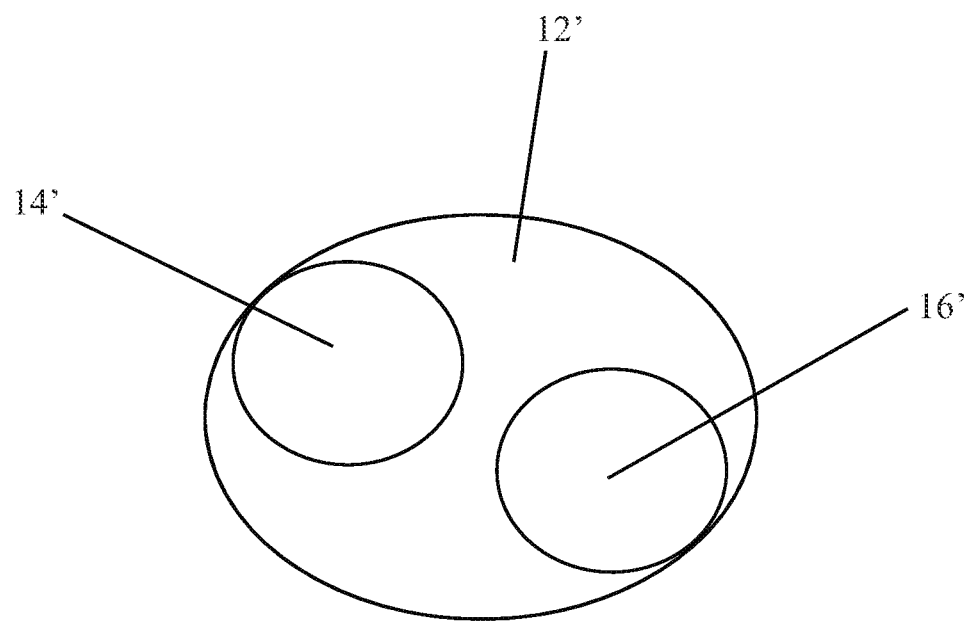
FIG. 9 is a top plan view of another embodiment of a multiple-orifice valve assembly of the invention.

The first and second orifices 14, 16 are spaced from each other across the width of the valve frame 12, and the spacing and exact orientation of the orifices 14, 16 can be selected to provide desired performance characteristics for the valve. For example, the orifices 14, 16 can be generally circular in shape and arranged relative to their valve frame 12 so that the center points of the orifices 14, 16 generally coincide with a central axis that runs across the width of the valve frame 12. However, it is understood that the orifices 14, 16 can be at least slightly offset relative to the central axis of the valve frame 12 and/or that they can be at least slightly offset relative to each other (e.g., FIG. 9 illustrates an alternative valve assembly including first and second orifices 14', 16' slightly offset relative to a central axis of valve frame 12'). The orifices 14, 16 can be at least slightly spaced from each other, as shown, thereby providing a central area of the valve frame 12 between the two orifices 14, 16. Preferably, the portions of the heart valve assembly 10 between the orifices is impermeable to blood flow to resist regurgitation. The illustrated space between the orifices 14, 16 is one exemplary configuration, and can be smaller or larger than shown. Alternatively, there may be no space between two adjacent orifices 14, 16. Longitudinal axes that extend through the orifices (generally in the direction of blood flow) can be generally parallel to each other such that the orifices and corresponding valves lie in the same plane. Alternatively, the longitudinal axes of the orifices may be at least slightly offset relative to each other so that the orifices are at least slightly tilted or tipped toward or away from each other within the valve frame (e.g., as shown in FIG. 9).

As discussed above, in the exemplary embodiment of FIGS. 1 and 2, the valve frame 12 includes two tri-leaflet valves 18, 20. In order to provide the structure for attachment of these valves, multiple commissure posts 28 extend from the first side 24 of the valve frame 12. In particular, three commissure posts 28 are positioned around each of the orifices 14, 16, where the posts 28 can be spaced generally evenly from each other around the orifices 14, 16, or they can be unevenly spaced, depending on the characteristics of its corresponding valve. The commissure posts can be rigid yet somewhat flexible structures, which can be covered with a cloth-like material. The commissure posts define the juncture between adjacent tissue or synthetic leaflets that are secured within an orifice.

The valves provided in the valve frames described herein may use a preserved bovine jugular vein of the type described in the above-cited Bonhoeffer, et al. and Tower, et al. references. However, other vessels or donor species may alternatively be used for various reasons. For example, in order to provide additional valve strength in the relatively high-pressure conditions that exist in the mitral valve area of the heart, pericardial valves, polymeric valves, or metallic valves may alternatively be used in a tricuspid or bicuspid leaflet configuration.

FIG. 3 illustrates another embodiment of a double orifice implantable heart valve 30, which includes two prosthetic valves 32, 34 surrounded by a valve frame 36. In this embodiment, valves 32, 34 can each include stent structures of the type used in areas of the heart that accommodate relatively small, circular valves, such as the pulmonic valve. The valve frame 36 may be a gasket or other member that surrounds the outermost periphery of the valves 32, 34 to provide for sealing against paravalvular leakage and to facilitate pannus in-growth for stabilization of the heart valve 30. The valve frame 36 also preferably provides enough structural strength to position and maintain the valves 32, 34 in their desired arrangement relative to each other. The frame 36 can be relatively rigid to prevent most or all movement of the valves 32, 34 relative to each other, or the frame 36 can be relatively flexible to allow at least some movement of the valves 32, 34 relative to each other.

Another embodiment of a double orifice implantable valve assembly 100 is shown in FIG. 6. Valve assembly 100 includes a frame 102 from which two pairs of commissure posts 104 extend. Each commissure post 104 is positioned with another commissure post 104 located across from it on generally the opposite side of the frame 102. Each pair of commissure posts 104 provides the attachment areas for a bi-leaflet valve, where the frame 102 illustrates a first bi-leaflet valve 106 and a second bi-leaflet valve 108. As shown, valves 106, 108 are attached directly to the frame 102 in such a way that they do not have their own frames or stents. The valves can thus contact each other at least slightly in the central area of the stent frame, as illustrated. Since there is no additional stent structure internal to the frame 102, the size of the valves can be maximized relative to the opening in the frame 102.

The individual valves of the double orifice implantable heart valves described herein are generally shown and described as being cylindrical in shape; however, a number of different stent shapes are also contemplated, such as valves that are oval or elliptical in shape. Another exemplary alternative configuration is illustrated in FIG. 4 with a double orifice implantable heart valve 50 that includes a first prosthetic valve 52 and a second prosthetic valve 54, both of which are surrounded by a valve frame or gasket 56. Each of these two valves 52, 54 has a curvilinear surface that can be designed to generally match the shape of the ends of the annulus of a mitral valve, and a generally flat or planar surface that results in more "squared off" corners where the flat surface meets the curvilinear surface. The flat surfaces of the valves 52, 54 are in contact with each other along at least a portion of their lengths at a central area 58. This arrangement provides for less gaps or openings between the individual valves in a multiple valve arrangement than when circular valves are used. The heart valve 10 of FIG. 1 may alternatively include orifices that are shaped similarly to the valves 52, 54 of this embodiment in order to utilize valves that are somewhat D-shaped.

Another exemplary configuration of an implantable heart valve assembly of the invention includes a valve frame having two or more individual valves having different sizes and/or shapes from each other. For example, one or both of the valves can be at least slightly elliptical, oval, D-shaped, square, or differently shaped in cross-section when in their expanded conditions. For another example, one of the valves within a valve frame can be at least slightly larger than the other valve or valves of that frame, which would correspond to the orifices in which they are attached. In some cases, the differently sized and/or shaped orifices can help to better adapt the multiple-orifice heart valve to the native valve opening. The shape of the valves can be designed and selected to provide a proper fit to the patient's anatomy.

Figure 7:
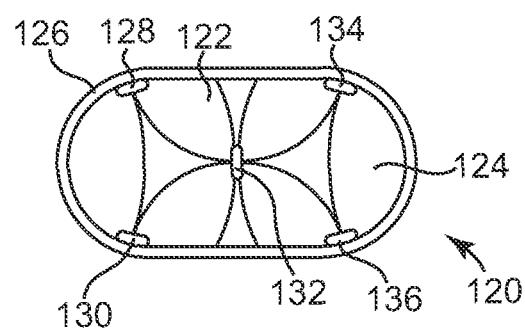
FIG. 7 is a top plan view of another embodiment of a multiple-orifice valve assembly of the invention.

Another exemplary multiple orifice valve assembly 120 is illustrated in FIG. 7. Valve assembly 120 includes a first valve 122 and a second adjacent valve 124, both of which are tri-leaflet valves positioned within a stent frame 126. Stent frame 126 includes a number of commissure posts extending from one of its surfaces that act as the attachment points for the leaflets of the valves 122, 124. In particular, the leaflets of valve 122 are attached at commissure posts 128, 130, 132, and the leaflets of valve 124 are attached at commissure posts 132, 134, 136. Thus, the relatively central stent post 132 is shared by both of the valves 122, 124, thereby providing a relatively large orifice size inside the stent frame 126 with minimal obstructions to blood flow. A similar configuration can alternatively be used with two bi-leaflet valves in a single stent frame, where one of the commissure posts of the assembly is common to both valves. In yet another alternative embodiment, a stent assembly may include one bi-leaflet and one tri-leaflet valve, where both of the valves share one common commissure post.

Figure 8:
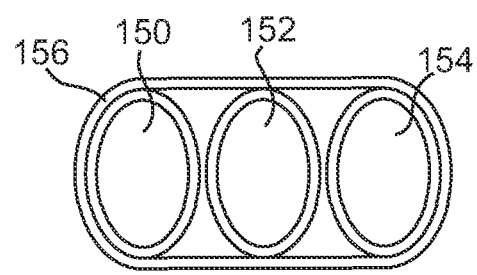
FIG. 8 is a top plan view of a tri-orifice valve assembly of the invention.

Other valve assembly arrangements can include more than two valves within a single stent frame, as is contemplated by the present invention. For one example, three valves 150, 152, 154 are illustrated within a stent frame 156 in FIG. 8. The valves 150, 152, 154 are shown as having an intermediate stent or strut portion between each two adjacent valves; however, any of the other features described herein relative to stent assemblies with two valves can also be utilized in stent frames with three or more valves. Such multiple valve assemblies can include bi-leaflet valves, tri-leaflet valves, combinations of bi- and tri-leaflet valves that do not include intermediate strut portions, and the like.

Once a valve frame of the invention having attached valve structures (e.g., one of the prosthetic heart valve with multiple orifices described above) is implanted within the patient, the valve can function for a period of time with no noticeable issues. However, if deficiencies occur at any time after implantation in one or more of the valves of the multiple-valve structure, each deficient valve can be replaced by percutaneously delivering a new valve via transcatheter implantation. The invention further includes a method of surgically implanting a multiple orifice valve assembly into the mitral valve area of a patient, then percutaneously delivering a replacement valve to at least one of the orifices of the surgically implanted valve assembly. Each of these individual valves would be relatively small as compared to the overall valve size that would be required for percutaneous implantation of a comparable mitral valve that fills the mitral valve space, thereby better facilitating percutaneous implantation through a variety of access sites. The replacement valve can be a stented valve that includes an outer stent structure to which a valve structure is attached.

FIG. 5 illustrates a distal portion of an exemplary delivery system 70 as it is delivering a replacement stented valve 72 (shown schematically as only a stent of the valve) to a double orifice heart valve 80 that is depicted by two adjacent heart valves 74, 76. Heart valves 74, 76 are the two orifices of the double orifice heart valve 80 of the invention. The device or structure that attaches these valves to each other is gasket or frame 78. That is, the heart valves 74, 76 are intended to represent the two orifices of a single structure 80 that would previously been implanted into a patient, where the single structure could have been implanted to replace a mitral valve, for example. FIG. 5 represents the situation where some failure or malfunction of the leaflets of heart valve 74 has occurred, thereby necessitating a replacement of that heart valve. In accordance with the invention, it is possible to replace only this valve 74 of the two-valve system with a replacement stented valve 72, although it may be desirable or necessary to replace both valves 74, 76 with new replacement stented valves. The valve replacement procedure can advantageously be accomplished using a percutaneous valve delivery system.

In order to reduce potential stresses on the valve frames described herein and to reduce potential stresses on the associated annulus, it is also possible to provide multiple orifice structures that can move at least slightly relative to each other within a single native opening. In particular, the valves may be moveable relative to a defined plane and/or may be moveable to be positioned closer or further from each other during and after implantation. In such an embodiment, the stent frames can be made of flexible materials, such as metals, (e.g., Nitinol), polymers, or tissue-based materials.

The stented valves used to replace a deficient valve using the methods of the invention can correspond generally to a stent of the type described in the above-cited Tower, et al. and Bonhoeffer et al. references, for example, although it is understood that a wide variety of stent configurations can be used in accordance with the invention. The replacement stented valves may include a stent structure that is fabricated of platinum, stainless steel, Nitinol, an alloy of the type commercially available under the trade designation MP35N, or other biocompatible metal. The replacement stented valves may alternatively be fabricated using wire stock as described in the above-cited Tower, et al. applications, or the stented valves may be produced by machining or laser cutting the stent from a metal tube, as is commonly employed in the manufacturing of stents. The number of wires, the positioning of such wires, and various other features of the stents can vary considerably from that shown in the figures. In another alternative, the valves used to replace a deficient valve may be stentless valves.

In any case, the replacement stented valves used in the methods of the invention are preferably compressible to a relatively small diameter for insertion into a patient, but are also at least slightly expandable from this compressed condition to a larger diameter when positioned in a desired location in the patient. It is further preferable that the process of compressing the stented valves does not permanently deform the stent in such a way that expansion thereof would be difficult or impossible.

Any of the stent assemblies discussed herein can further include structures that provide a fixation function for securing the stent assembly in its desired location relative to the orifice of a previously implanted heart valve. For example, the stent assembly can include hooks, barbs, or the like that attach to a structure of a valve orifice upon deployment of the stent assembly.

A portion of an exemplary system that can be used to implant a stented valve of the types described above includes an elongated balloon catheter having an inflatable balloon that is connected for fluid communication with a lumen that extends through the length of the catheter. The lumen provides for inflation and deflation of the balloon with a fluid, such as a radio-opaque fluid, during the process of deploying a stented valve within a patient. The delivery system may include a thin guide wire that extends generally along the length of the catheter, which may be used in a conventional manner to guide the catheter to its desired implant location. When the components of the system are positioned relative to the orifice of a patient, a balloon may be inflated to thereby expand the stent to the desired size relative to the orifice in which it will be positioned. After such stent expansion is complete, the balloon can be deflated and the system can then be withdrawn from the patient.

It is further contemplated that two or more percutaneous valves can be simultaneously or sequentially delivered to a multiple orifice stent using a delivery system that has multiple balloons. For example, if both valves of a double-orifice valve are to be replaced at the same time, a delivery system having two balloons can be used to deliver both valves simultaneously.

The replacement heart valves, along with the multiple-orifice implantable heart valves of the present invention may be positioned within the desired area of the heart via entry in a number of different ways. In one example, the valves may be inserted transatrially, where entry may be done either percutaneously or in a minimally invasive technique on a beating heart in which access is through the side of the heart, or even through a standard open heart valve replacement procedure using heart-lung bypass and sternotomy where the described device would be used as an alternative to the standard replacement. In another example, the valves may be inserted transapically, where entry again may be done either percutaneously or in a minimally invasive technique on a beating heart in which access is through the side of the heart. In yet another example, the valves may be inserted transeptally, where entry can be done percutaneously, such as via the venous system into the right atrium and across a small hole in the septum to enter the left atrium. In yet another example, the valves may be inserted transfemorally through the arterial system. It is also possible that the delivery approaches may include balloons that would be used to facilitate the crossing of the mitral valve, thereby avoiding entanglement in the mitral apparatus.

It is also contemplated that the stented valves of the present invention are self-expanding such that pressure is required to maintain the valve in its compressed condition, and removal of such pressure will allow these stented valves to expand to their desired size. In these cases, the delivery system will be somewhat different than that described above relative to stents that are not self-expanding, and will instead include a system that only requires removal of external pressure (e.g., a compressive sheath) to allow the stented valves to expand, such as is the case with the delivery of stent grafts for aneurysms in the ascending aorta. These systems may also incorporate means for recapturing and/or repositioning the stented valve, if desired. In any case, it may be desirable to measure the mitral valve area with some type of spacer prior to installing the actual stent assembly in the heart of the patient.

The stented valves may further include a means of facilitating orientation of the assembly relative to the orifice in which they will be implanted, which can be particularly advantageous in cases where the stented valves include asymmetric features and configurations that must be properly oriented relative to the anatomy of the patient. To that end, the stented valves may include portions with materials that are opaque when viewed with various imaging techniques, such as echogenic coatings and radiopaque metals and polymers. Additionally or alternatively, the material used to fabricate the stent itself may be highly visible when using certain imaging techniques so that the user has a clear visibility of the orientation of the device prior to and during deployment.

The present invention has now been described with reference to several embodiments thereof. The foregoing detailed description and examples have been given for clarity of understanding only. No unnecessary limitations are to be understood therefrom. It will be apparent to those skilled in the art that many changes can be made in the embodiments described without departing from the scope of the invention. Thus, the scope of the present invention should not be limited to the structures described herein.

What is claimed is:

1. A heart valve assembly for implantation in a body lumen, the heart valve assembly comprising:
   a percutaneously implantable valve frame comprising an outer periphery having both a first side and an opposite second side, wherein the first side is an upper side of the valve frame and the second side is a lower surface of the valve frame; further wherein the valve frame has an outer shape that is compatible with a shape of a mitral valve;
   at least one opening extending through the valve frame from the first side to the second side, the at least one opening including a first opening;
   wherein the first opening is defined by an inner frame surrounded by the valve frame, and further wherein a perimeter shape of the first opening differs from a perimeter shape of the valve frame, and further wherein the first opening is offset with respect to a central axis of the valve frame; and
   a tissue valve disposed within the first opening, the tissue valve has a curvilinear surface and a generally flat surface collectively forming a substantially D-shape matching at least a portion of the annulus of the mitral valve.

2. The heart valve assembly of claim 1, wherein the valve frame has a structural strength capable of surgical implantation into a patient.

3. The heart valve assembly of claim 1, wherein the valve frame is a gasket that surrounds the outermost periphery of the tissue valve to provide for sealing against paravalvular leakage and to facilitate pannus in-growth for stabilization of the heart valve assembly.

4. The heart valve assembly of claim 1, wherein one portion of the D-shape is planar and is in contact with an inner planar surface of the first opening.

5. The heart valve assembly of claim 1, wherein the curvilinear surface of the D-shape is in contact with an inner curvilinear surface of the first opening.

6. The heart valve assembly of claim 1, further comprising at least two commissure posts extending from the first side of the valve frame and adjacent to the first opening, wherein the tissue valve is coupled to the at least two commissure posts.

7. The heart valve assembly of claim 1, wherein the at least one opening further includes a second opening apart from the first opening.

8. The heart valve assembly of claim 7, further comprising a second tissue valve disposed within the second opening.

9. The heart valve assembly of claim 7, wherein the first opening and the second opening are offset with respect to each other.

10. A heart valve assembly for implantation in a body lumen, the heart valve assembly comprising:
    a percutaneously implantable valve frame comprising an outer periphery having both a first side and an opposite second side, wherein the first side is an upper side of the valve frame and the second side is a lower surface of the valve frame; further wherein the valve frame has an outer shape that is compatible with a shape of a mitral valve;
    a first opening and a second opening; each of the first and second openings extending through the valve frame from the first side to the second side;
    wherein the first opening is defined by an inner frame surrounded by the valve frame, and further wherein a perimeter shape of the first opening differs from a perimeter shape of the valve frame, and further wherein the first opening and the second opening are offset with respect to a central axis of the valve frame; and
    a first tissue valve disposed within the first opening.

11. The heart valve assembly of claim 10, wherein the first opening and the second opening are offset with respect to each other.

12. The heart valve assembly of claim 10, wherein the first tissue valve has a curvilinear surface and a generally flat surface collectively forming a substantially D-shape matching at least a portion of the annulus of the mitral valve.

13. The heart valve assembly of claim 10, further comprising a second tissue valve disposed in the second opening.

* * * * *